US009202067B2

(12) United States Patent
Gramelspacher et al.

(10) Patent No.: US 9,202,067 B2
(45) Date of Patent: *Dec. 1, 2015

(54) CONTROLLING AN ANALYSIS SYSTEM OF BIOLOGICAL SAMPLES

(71) Applicant: Roche Diagnostics Operations, Inc., Indianapolis, IN (US)

(72) Inventors: Lothar Gramelspacher, Zurich (CH); Andrzej Knafel, Walchwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,599

(22) Filed: Feb. 26, 2015

(65) Prior Publication Data

US 2015/0178508 A1 Jun. 25, 2015

Related U.S. Application Data

(63) Continuation of application No. 13/899,732, filed on May 22, 2013, now Pat. No. 8,996,878.

(30) Foreign Application Priority Data

Jun. 13, 2012 (EP) .................................. 12171721

(51) Int. Cl.
*G06F 21/00* (2013.01)
*G06F 21/60* (2013.01)
(Continued)

(52) U.S. Cl.
CPC ............ *G06F 21/602* (2013.01); *A61B 5/7285* (2013.01); *G06F 19/322* (2013.01); *G06F 21/31* (2013.01); *G06F 21/335* (2013.01); *G06F 21/36* (2013.01)

(58) Field of Classification Search
CPC ................................................ G06F 21/602
USPC ........................................................ 713/183
See application file for complete search history.

(56) References Cited

U.S. PATENT DOCUMENTS 5,633,932 A 5/1997 Davis et al.
7,661,127 B2 2/2010 Hirsch
(Continued)

FOREIGN PATENT DOCUMENTS

EP 2037651 A1 3/2009
JP 2005-190447 A 7/2005

OTHER PUBLICATIONS

Naedele, Martin, "An Access Control Protocol for Embedded Devices," Industrial Informatics, IEEE, 2006, pp. 565-569.

*Primary Examiner* — Peter Shaw
(74) *Attorney, Agent, or Firm* — Roche Diagnostics Operations, Inc.

(57) ABSTRACT

A method for controlling an analysis system is presented. The method comprises receiving, by an encryption unit, authentication data of a user. In the case of a successful authentication, a user-specific security code is generated by the encryption unit. The security code is outputted by the encryption unit to the authenticated user. The security code and the user-ID are received by an authentication unit coupled to the analysis system via a user-interface coupled to the authentication unit. The security code is decrypted by the authentication unit. If the decrypted security code matches with the user-ID, the user is authenticated at the authentication unit and an authentication signal is generated by the authentication unit for permitting the user to initialize at least one function of the analysis system.

15 Claims, 5 Drawing Sheets

(51) Int. Cl.
*G06F 21/33* (2013.01)
*G06F 21/31* (2013.01)
*A61B 5/00* (2006.01)
*G06F 19/00* (2011.01)
*G06F 21/36* (2013.01)

(56) References Cited

U.S. PATENT DOCUMENTS

| | | |
|---|---|---|
| 8,087,062 B2 | 12/2011 | Koeda |
| 2003/0061492 A1 | 3/2003 | Rutz et al. |
| 2008/0184330 A1 | 7/2008 | Lal et al. |

CONTROLLING AN ANALYSIS SYSTEM OF BIOLOGICAL SAMPLES

CROSS-REFERENCE TO RELATED APPLICATIONS

This application is a continuation of U.S. application Ser. No. 13/899,732, filed May 22, 2013, now allowed, which is based on and claims priority to EP 12171721.9, filed Jun. 13, 2012, which is hereby incorporated by reference.

BACKGROUND

The present disclosure generally relates to the field of analysis systems for analyzing biological samples and, in particular, to the control of analysis systems.

Laboratory devices, in particular analysis systems used for analyzing biological samples, must be closely controlled to ensure that the returned analysis results are correct. To an increasing degree, analysis systems are complex multi-component devices which need to be configured and maintained by specially trained personnel. In particular, the tasks such as configuring, maintaining and/or repairing analysis systems are often executed by external technical personnel such as, field service representatives (FSRs).

In order to prohibit non-expert users from accidentally modifying a well-established configuration of an analysis system and/or from triggering a function of the analysis system which may cause harm to the system or the analyzed samples, access to functions of an analysis system must be tightly controlled to ensure that sensitive configuration data and functions of an analysis system can only be accessed by a specially trained user. In a further aspect, access to Protected Health Information (PHI), for example, patient data created as a result of an analysis, by an unauthorized user (e.g. a FSR) needs to be prohibited.

In prior art systems, a centralized database comprises data indicative of the user(s) having access rights to one or more network-connected laboratory instruments. A problem of this approach is that many laboratory devices are not connected to the internet or an intranet and are therefore unsuited for a centralized, network-based authentication system.

Other laboratory devices relying on 'prestored' authentication data may selectively allow an authenticated user to access functions of the devices. Authentication data stored locally in a plurality of laboratory devices may be distributed over different laboratories or even different cities or countries. Thus, de-centrally storing authentication data tends to be highly inflexible and insecure. Centrally stored, static passwords may be hacked or illicitly passed to unauthorized persons. In the case a field representative or other technically skilled user leaves a company, it may be highly time consuming or even impossible to change the user's authentication data in all devices affected.

Therefore, there is a need for an improved method for controlling an analysis system involving an authentication of a user such as, for example, a non-standard user such as, a FSR, for example, who logs into the system only infrequently or in the event of a malfunction.

SUMMARY

According to the present disclosure, a method and system for controlling an analysis system is presented. The analysis system can comprise an analyzer for analyzing biological samples. A user-ID of a user and authentication data of the user for authenticating the user at an encryption unit can be received by the encryption unit. In the case of a successful authentication at the encryption unit, a user-specific security code can be generated by the encryption unit using an encryption algorithm, thereby taking the user-ID as input. The user-ID can be stored in the security code only in encrypted form. The security code for providing the security code to the authenticated user can be outputted by the encryption unit. The security code and the user-ID can be received by the authentication unit coupled to the analysis system via a user-interface coupled to the authentication unit. The security code and the user-ID can be entered by the user. The authentication unit can enable access of the user to the analysis system. The security code can be decrypted by the authentication unit and if the decrypted security code matches with the user-ID can be determined. The matching can encompass a check if the security code comprises the user-ID in encrypted form. If the decrypted security code matches with the user-ID, the user can be authenticated at the authentication unit and an authentication signal can be generated by the authentication unit for permitting the user to initialize at least one function of the analysis system.

Accordingly, it is a feature of the embodiments of the present disclosure to provide an improved method for controlling an analysis system involving an authentication of a user such as, for example, a non-standard user. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
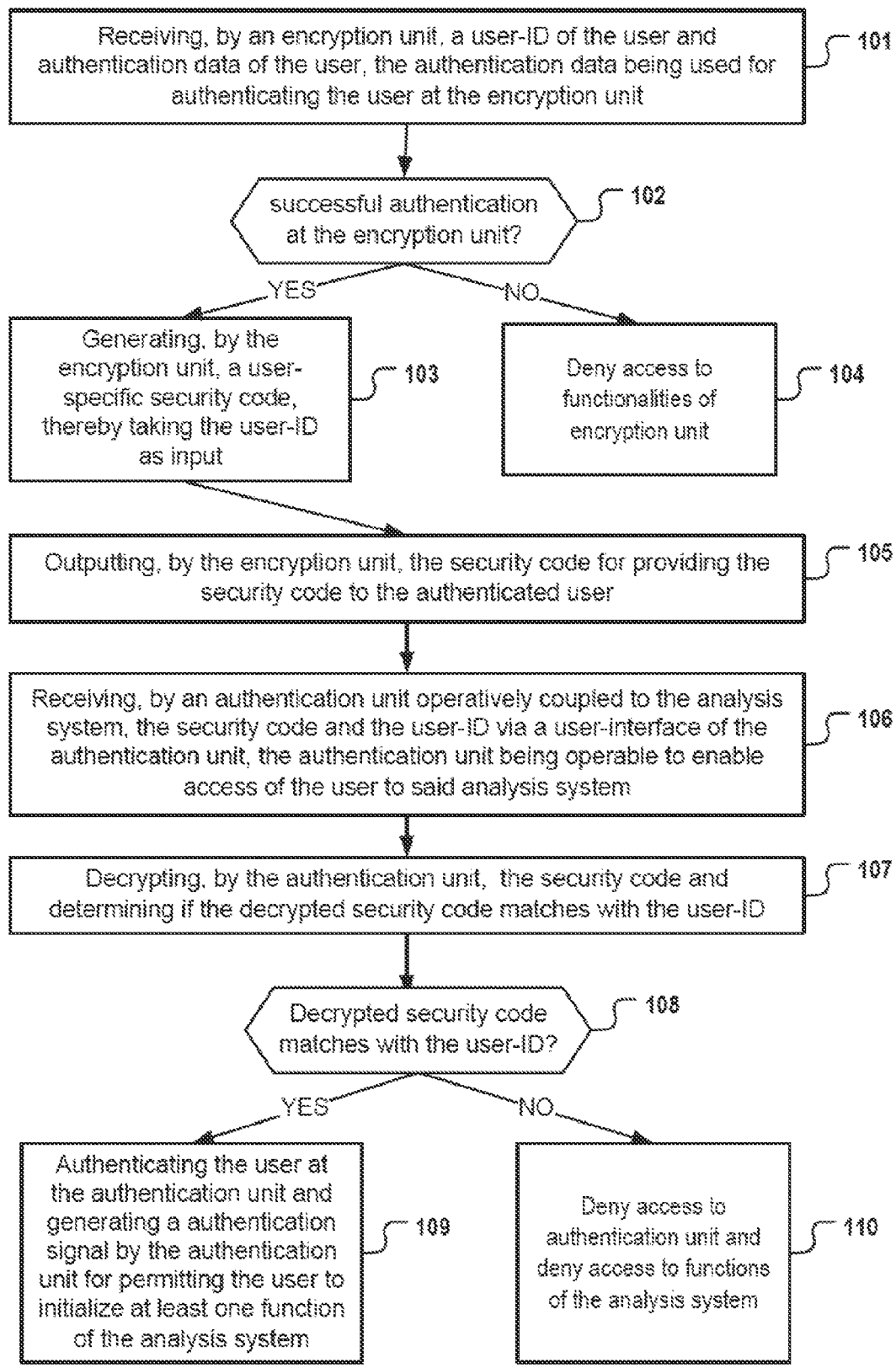
FIG. 1 illustrates a flowchart of a method for controlling an analysis system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A 'user' as used herein can be a human being who can be represented and identified by a user-ID uniquely assigned to the user. The user may have registered at a program logic part of or coupled to an encryption unit. The user may be a FSR. A group of users having the same user role and permissions in respect to one or more analysis system may be represented by the same user-group-ID and can in the following be subsumed under the term 'user'.

A 'biological sample' or 'sample' as used herein can be a quantity of biological material, such as blood, urine, saliva, or the like, for use in laboratory analyses.

The term 'analyzer' as used herein can encompass any apparatus or apparatus component that can induce a reaction of a biological sample with a reagent for obtaining a measurement value. An analyzer can determine via various chemical, biological, physical, optical or other technical procedures a parameter value of the sample or a component thereof. An analyzer may measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types.

An 'analysis system' as used herein can encompass a control unit coupled to one or more analyzers that can be part of the analysis system. The control unit can control the performance of an analysis by any one of the analyzers. In addition, the control unit may evaluate and/or process gathered analysis data, to control the loading, storing and/or unloading of samples to and/or from the analyzer, to initialize an analysis or hardware or software operations of the analysis system used for preparing the samples, sample tubes or reagents for the analysis and the like.

An 'encryption unit' as used herein can be any hardware-, firmware- and/or software-based module to execute program logic for encrypting input data and returning an encrypted data value. Depending on the embodiment, different encryption algorithms may be used. The encryption unit may comprise or coupled to a man-machine interface, for example, a graphical user interface (GUI), for receiving the input data, for example, a user-ID of a user.

An 'extended analysis system' as used herein can be a system comprising one or more analysis systems and an encryption unit, whereby the encryption unit can be decoupled from any of the analysis systems. Being 'decoupled' may imply that there does not exist any network connection or other data exchanges between the encryption unit and any of the analysis systems, or that an existing network connection cannot be used for data exchange.

An 'authentication unit' as used herein can be any hardware-, firmware- and/or software-based module to execute program logic for receiving and processing a security code for determining, in dependence on the processing, if the user providing the security code has successfully authenticated at the analysis system to which the authentication unit can be coupled. Each analysis system can comprise or coupled to one single authentication unit.

A unit being 'coupled' to an apparatus can be a unit which can be part of the apparatus or can exchange data with the apparatus via a network connection, for example, an intranet or internet.

The expression 'authentication data' as used herein can encompass any data which can allow the user to authenticate at the encryption unit or can be indicative of an already accomplished successful authentication of the user at the encryption unit or at the runtime environment of the encryption unit. A runtime environment can be a software component designed to support the execution of computer programs written in some computer language. The run-time system can contain implementations of basic low-level commands and may also implement higher-level commands and may support type checking, debugging, and even code generation and optimization. The runtime environment may be, for example, the operating system of a computer hosting the encryption unit or may be a virtual machine. For example, the user may authenticate at the computer hosting the encryption unit by biometric data of the user, by a password or similar methods to prove the identity of the user. Biometric data may be a fingerprint, a face print, a voice print, or the like being characteristic for the user.

Likewise, any call for starting or executing the encryption unit by a user having authenticated at the runtime environment of the encryption unit may be considered as a provision of authentication data provided the call can be permitted to users having authenticated at the runtime environment.

A 'user-ID' as used herein can be a unique, sequence of characters particular to a user and can be used to identify the user at one or more analysis systems and corresponding authentication units and at the encryption unit. In particular, the user-ID may be a secret character sequence comprising alphanumeric or special characters or a mixture thereof, for example, a password or a PIN. The user-ID may be entered by the user via a man-machine interface such as a keyboard, a touch-screen, and/or a mouse in combination with a graphical user interface.

A 'security code' as used herein can be a data pattern derived from the user-ID by an encryption algorithm. Depending on the embodiment, the security code may be a human-readable code, for example, a character string, and/or a machine-readable code. The security code may be an optically readable code, for example, a matrix code, a bar code, a QR code, or a data value stored to a portable medium such as an USB-stick, a storage medium of a mobile phone, a memory unit of an RFID chip, or the like.

A method for controlling an analysis system involving an authentication of a user at the analysis system is provided. The analysis system can comprise an analyzer for analyzing biological samples. The method can comprise receiving, by an encryption unit, a user-ID of the user and authentication data of the user for authenticating the user at the encryption unit. In the case of a successful authentication at the encryption unit, a user-specific security code can be generated by the encryption unit taking the user-ID as input. The security code for providing the security code to the authenticated user can be outputted by the encryption unit. The security code and the user-ID can be received by an authentication unit coupled to the analysis system via a user-interface coupled to the authentication unit. The authentication unit can enable access of the user to the analysis system. The coupled user-interface may be located locally (that is, by the computer system hosting the authentication unit) or remotely (that is, by a computer system not hosting the authentication unit). The security code can be decrypted by the authentication unit and can be determined if the decrypted security code matches with the user-ID. If the decrypted security code matches with the user-ID, the user can be authenticated at the authentication unit and a authentication signal can be generated by the authentication unit for permitting the user to initialize at least one function of the analysis system.

The term 'decrypting' as used herein can be understood as "applying cryptographic algorithms in context of secure communication and signature verification" but not in the context of hiding or pseudonymizing information for the purpose of information confidentiality.

Matching a security code with the user-ID as used herein can encompass a comparison of the security code and the user-ID or a comparison of respective derivative values. The details of the operation depend on the used encryption algorithm. According some embodiments, the comparison can be or can involve a check if the security code comprises the user-ID in encrypted form.

The features may be advantageous as the authentication scheme does not require storing any user-ID or other authentication information locally at the individual analysis systems. As the analysis systems are usually not connected to any network, the features may allow updating user-specific permissions in respect to individual analysis systems and/or individual functions of the analysis systems centrally at the encryption unit without having to update and data stored locally at or within the 'isolated' analysis systems. Thus, the task of keeping user-IDs of registered users and respective permissions up-to date can be significantly facilitated. As any change to the list of 'known' user-IDs and corresponding permissions may need to be updated only once at the site of the encryption unit but not at the site of any of the authentication units/analysis systems, the time required for granting and withdrawing permissions to or from individual users may be greatly shortened. This may also increase the security of the authentication process as in case authentication data, for example, a user's password, was stolen or was otherwise exposed to untrustworthy third parties, access to all affected analysis systems can quickly be blocked by updating the requirements in respect to the authentication data of the user at the site of the encryption unit, for example, by assigning the user a new password for authenticating at the encryption unit. The stolen or lost password cannot be used any more for generating a security code for logging into an analysis system. Thus, a flexible, centrally manageable authentication system for one or more analysis systems may allow a user to authenticate, by the security code, at one or more analysis systems without necessitating the operator to modify each of the affected analysis systems locally and without the necessity to connect the individual analysis systems to the central encryption unit via a network.

According to an embodiment, the encryption unit can receive the authentication data of the user via a network, for example, the internet or an intranet.

According to an embodiment, the analysis system and the authentication unit may not be connected to the internet. The analysis system may are also not be connected to an intranet of the laboratory operating the analysis system.

According to an embodiment, the security code and the user-ID entered by the user in the authentication unit for authenticating at the analysis system can be deleted after a successful authentication of the user at the authentication unit. The authentication unit may not comprise and cannot be connected to any non-transitory data storage comprising the security code or any other kind of data allowing the authentication of the user at the authentication unit and the corresponding analysis system. These features can be advantageous as the security is increased (data for authentication management stored only once at the site of the encryption unit can be protected from unauthorized access than data stored in multiple copies on multiple analysis systems) and the task of keeping the data up-to-date can be facilitated.

According to an embodiment, upon a successful authentication of the user, the user-ID can be passed to the analysis system. The analysis system may store the user-ID in a log-file or audit-trail or the like.

According to embodiments the at least one function can be selected from a group comprising: analyzing the biological samples; analyzing quality control or calibration samples wherein some of the quality control or calibration samples may be biological test samples, i.e., biological samples, such as, for example blood or urine samples, which can be analyzed in order to evaluate the correctness of the analysis procedure, but not in order to determine biomedical parameters, such as. For example, metabolite levels, hormone levels, and the like of a patient; executing a maintenance function, a maintenance function being a function for detecting and/or repairing errors of the analysis system or bottlenecks in a sample processing workflow executed by the analysis system such as, for example, misplaced sample tubes or reagents blocking the analysis system may be removed wherein a maintenance function can be a function for ensuring, re-establishing or improving the ability of the analysis system to analyze the biological samples; triggering system-diagnostic functions of the analysis system for generating an error report by the analysis system such as, for example, analysis results may be compared with reference values, the fill-level of reagents may be checked, and the like; un-locking a reversibly lockable hardware component of the analysis system for permitting the user to access the hardware component such as, for example, an opening allowing to load or unload biological samples to or from the analysis system may be un-locked upon a successful authentication; replenishing solid consumables of the analysis system or permitting the user to replenish the solid consumables, for example, pipettes, pipet tips, cuvettes, reaction containers, and the like; refilling liquid consumables (reagents, controls, calibrators, etc.) of the analysis system or permitting the user to refill the liquid reagents; updating an application program used for maintaining or controlling the analysis system or permitting the user to execute the update; repairing an error state of the analysis system or permitting the user to execute the repair; execute a calibration by the analysis system or permitting the user to execute the calibration; execute a firmware-update or software-update by the analysis system or of its components or permitting the user to execute the update; permitting the user to access a data storage of the analysis system wherein the data storage can comprise data necessary for maintaining the analysis system; executing a washing or cleaning operation by the analysis system or permitting the user to execute the washing or cleansing operation; configuring parameters of an application program monitoring or controlling the analysis system; executing inventory functions, for example, counting remaining tests, remaining test samples or remaining volume of reagents or sample; installing, adding or removing hardware components of the analysis system; and defining new rules or modifying rules for processing the biological samples.

Multiple kinds of maintenance function and system-diagnostic functions can exist which depend on the type of the analysis system (e.g. IC/ECL, CC, and MD) used. System Self Checks of "IC/ECL analytical systems" may include, among others: Artificial media (AM) tests (reference media checks ('blank checks'), serum albumin P component (SAP)-beads binding Biotin and Ruthenium labeled antibody (AB)-checks, bead carry over checks, pipetting precision checks), Thyrotropin (TSH) tests (measurement cell check—determination of slope between two calibrators with different concentration provides information about quality of measurement cell, deviation of 1st value max. 10% of following values, with and without pre-wash); and High voltage tests (max. electrochemical luminescence, photomultiplier adjustment and/or reference cell ('blank cell') tests).

Calibration checks of "IC/ECL analytical systems" may include, among others, a master calibration test (6-point calibration using Rodbard four parameter general curve fit function; or a 2-point calibration specific for calibrator and rackpack-lot).

Executing analyses of quality control samples of "IC/ECL analytical systems" may include the use of an analyte for verification/validation of calibration, pathological and non-pathological sample analysis (e.g. TroponinT), etc.

A maintenance function may comprise a flow check of a pipetted liquid, a pressure check, a cuvette check (of every empty cuvette, of a cuvette comprising a reference liquid, e.g. water, and checking if an obtained measurement value lies within a certain range), bubble detection, and the like.

These features may be advantageous as the user can be allowed or prohibited from executing or triggering functions of the analysis system or any of its components. The components may be the analyzer, a conveyor belt or robotic arm loading or unloading biological samples to and from the analysis system or the analyzer, reagent containers, and/or application programs controlling the analyzer and/or evaluating a biomedical analysis. By providing and blocking the user access on a per-function basis, a fine-grained access control may be provided.

According to an embodiment, the security code can comprise a signature of the user-ID or a derivative thereof. The signature can be generated by a private key stored in a first storage medium coupled to the encryption unit. Determining if the security code matches with the user-ID can comprise validating the signature. The validation can comprise decrypting, by a public key stored in a second storage medium coupled to the authentication unit, the received security code. The private and the public key may form an asymmetric cryptographic key pair. Using a signature can be advantageous as the signature can provide an additional level of security. The signature may comprise a certificate of a certification authority, thereby providing a further level of security.

According to an embodiment, outputting the security code can comprise generating, by the encryption unit, a printout displaying the security code and/or displaying, by the encryption unit, the security code on a screen. Receiving the security code by the authentication unit can comprise receiving the security code via a user interface. The user interface may be a graphical user interface (GUI) displayed on a screen coupled to the authentication unit. The security code can be a string manually entered in an entry field of the graphical user interface. These features may be advantageous as the user, for example, a field service representative, may be enabled to generate a printout of the security code, take the security code to the lab of a client and use it to authenticate at an analysis system at the client's side for maintaining or repairing the analytical system after having entered the security code for authenticating the user at the analysis system.

According to an embodiment, outputting the security code can comprise displaying, by the encryption unit, the security code on a display of a mobile processing device of the user and/or generating a printout displaying the security code. Receiving the security code by the authentication unit can comprise reading the displayed security code by a reader coupled to the authentication unit. The encryption unit may, for example, send the security code to the mobile phone of the user. The security code may be, for example, a 2-D code, for example, a bar code or a matrix code. The user may present the screen of his mobile phone displaying the security code to a reader (also referred herein as 'reader device') of the analysis system in order to provide the security code to the authentication unit of the analysis system. This may be advantageous as the security code can be transferred from the encryption unit to the authentication unit via the mobile processing device of the user fully electronically and without media discontinuity across the generating and the receiving instance.

According to an embodiment, the encryption unit can store the security code on a portable storage medium. The authentication unit can receive the security code from the user by a reader device of the analysis system reading the security code from the portable storage medium.

According to some embodiments, the security code can be transmitted and stored on a storage medium of a mobile phone of the user, whereby the mobile phone can display the security code on its screen and whereby the reader device can be an optical reader, for example, a camera. The security code may be a bar code or a matrix code or an alphanumerical string being processed by the encryption unit by an optical character recognition (OCR) function. According to some embodiments, the storage medium can be an RFID chip of the mobile phone of the user, whereby the mobile phone can comprise an RFID interface and whereby the reader device can be an RFID reader.

According to some embodiments, the reader device can be a reader device of the analysis system whose original function can be the identification of biological samples and/or reagent containers to be loaded into the analysis system. These features may be advantageous as no additional hardware component may be required in order to quickly and automatically enter the security code stored in the storage medium into the encryption unit. Reader devices used for identifying the samples and reagent containers may be, for example, optical readers, for example, bar code readers, RFID tag readers, or the like.

According to an embodiment, the security code can comprise the signature and an analysis system-type-ID indicative of a type of analysis system at which the authenticated user can be selectively allowed to execute the at least one function. This may be advantageous as a particular user, for example, a field service representative who is an expert in one particular kind of analysis system can be granted access to all analysis systems of that kind.

According to an embodiment, the security code can comprise the signature and an expiry date, i.e., a time value indicative of a date when the signature expires. This feature may be advantageous as using and evaluating an expiry date of the signature and the security code containing the signature can increase the security of the authentication schema. Users may have to authenticate at the encryption unit regularly in order to receive a new, valid code. Expired codes cannot be allowed access to the analysis system. According to an embodiment, the encryption unit can provide an interface, for example, a dialog window, allowing the user to enter the expiry date. Alternatively, the expiry date can be predefined by the encryption unit. The user-ID can be stored in the security code only in encrypted form as part of the encrypted section of the code.

According to an embodiment, the security code can comprise the signature and one or more property values, which can be selected, in any combination, from a group comprising: a time value indicative of a data when the signature expires; a key index indicative of a version of the private key used for generating the signature; a user-group-ID assigned a set of permissions for executing the at least one function and/or for accessing a data storage operatively coupled to the authentication unit; an analysis system-type-ID indicative of a type of analysis system by which the authenticated user can be selectively allowed to execute the at least one function; a region ID indicative of a geographic region wherein the analysis system can be located; and a function-ID indicative of the at least one function the user can be permitted to execute upon a successful authentication at the authentication unit.

The key index can be part of a non-encrypted section of the security code to allow selection of the proper key for decryption. A copy of the key index may in addition be stored in the encrypted part of the security code. The user-id can be encrypted and can become part of the encrypted code section. All other properties may be encrypted in the encrypted code section or in "clear text" in the un-encrypted sections of the code. For usability it may be ensured that the property values can be extracted directly as "clean text" or by a decryption key from the security code by the authentication unit. Encrypting the property values can increase the security level but may lengthen the generated security code. Storing the property values as clear text can be less protection against manipulated property values but can reduce the code length and thus can facilitate entering the security code.

According to an embodiment, the user can be a member of at least one of one or more user groups. Each of the user groups can have assigned a respective set of property values. When the security code is generated, the property values assigned to the at least one group can be automatically added to the security code. According to another embodiment, the user can be provided with a user-interface, for example, a GUI, for modifying one or more of the properties, for removing some of the property values and for adding additional property-values for creating a modified set of property values. The modified set of property values may then be included in the security code in the encrypted or in the non-encrypted code section.

According to an embodiment, the at least one function can be executed in accordance with the one or more property values of the security code. For example, the authentication unit may extract the properties from the received security code and may grant access to the at least one function of the analysis system in dependence on the extracted properties. For example, in case the security code comprises a property value indicative of a particular kind of analysis system, the authentication unit can grant access to its coupled analysis system only in case the analysis system is of the indicated kind of analysis system. In case a property value is indicative of one or more functions of the analysis system, the authentication unit can selectively grant access to the indicated functions. In case a property value is indicative of a geographic location, e.g. a lab, a city or a country, the authentication unit can selectively grant access to the indicated functions if its coupled analysis system currently resides within the geographic region. In case a property value is indicative of a date when the signature expires, the authentication unit can determines, by an electronic calendar accessible by the authentication unit, a current date and can selectively grant the user access to the at least one function if the current date does not lie after the expiry date of the signature. These features may be advantageous as the time and effort for communicating all the information from the encryption unit to the authentication unit can be reduced since the information is contained in the security code and as the authentication unit is operable to automatically extract the information from the security code, the user may not have to enter the information manually.

In case a property value is indicative of a key index indicative of a version of the private key used for generating the signature, the authentication unit can automatically select one of a plurality of public keys for decrypting the signature. The selection can be executed in dependence on the version of the private key, thereby selecting a public key that can form an asymmetric cryptographic key pair together with the private key indicated by the version. The encryption unit can use a plurality of private keys of different size for executing the encryption and the authentication unit can use a corresponding one of a plurality of public keys. Using long keys can increase the security but may increase the size of the security code generated and may thus also increase the time and effort for entering the code into the authentication unit manually. By supporting a plurality of keys of different size and indicating the used encryption key in the security code for allowing the authentication unit to automatically select the appropriate decryption key can be advantageous as it can be possible to select a key of a length appropriate for any one of a plurality of different use case scenarios. For example, in case a printout is generated and the user has to enter the security code manually, a short key may be used for encryption to keep the size (character sequence length) of the security code small. In case the security code is provided in form of a machine-readable code, for example, a bar code, a longer key providing a higher degree of security may be selected. According to an embodiment, the encryption unit can receive a selection of a data transmission technique for outputting the security code. The method may be the sending of a SMS, the sending of an e-mail or the generation of a print-out. The encryption unit can select the private key for executing the encryption in dependence on the selected method and can indicate the version of the selected private key by one of the property values of the generated security code. Alternatively, the used private key may be pre-configured.

According to some embodiments, the method can further comprises displaying, by the encryption unit, a dialog window to the user, the dialog window can allow the user to enter the user-ID and, upon entry of at least the user-ID, generating the security code and displaying at the dialog window the security code.

According to some embodiments, the outputting of the security code can comprise displaying, by the encryption unit, one or more GUI elements to the user, the GUI elements allowing the user to select one of a set of data transmission techniques comprising sending the security code via an SMS to a mobile processing device of the user; storing the security code on a portable storage medium, e.g. an USB-stick, a CD-ROM, Floppy disc, an external hard drive, an SD-card, a data storage of a chip card, or the like; generating a paper-based printout of the security code; and sending an e-mail to a mailbox of the user, the e-mail comprising the security code. These features may enable a user to flexibly select the one transmission technology being the best suited one for providing him the security code.

According to an embodiment, the user-ID can be a user-ID provided and managed by an operating system. The operating system can comprise a runtime environment of the authentication unit at the encryption unit. Enabling the user to execute the at least one function can be implemented as authenticating the user via the user-ID at the operating system. These features may be advantageous as they can reduce the number of authentication steps to be executed by the user at the analysis systems. Typically, current analysis systems already come with a data processing unit having an operating system at which a user can authenticate in order to execute some functions of the analyzer. Implementing the authentication at the authentication unit as an integral part of the log-in procedure for authenticating at the operating system of the analysis system can thus reduce the time required by the user to authenticate at the analysis system.

According to an embodiment, the authentication unit of the analysis system can be restricted to provide access to non-patient data only. 'Patient data' as used herein can be any data allowing the attribution of analysis results gathered by the analyzer to a patient's name. These features may be advantageous as FSRs or other persons not allowed access to sensitive biomedical patient data may selectively be allowed to access configuration data and/or anonymized analysis data. The analysis system may comprise a first and second data storage. The first data storage can comprise non-patient data, in particular technical information allowing the user to configure the analysis system or execute the at least one function in accordance with the technical information. The second data storage may comprise patient data. In case the matching returned as result that the signature is valid, the user can be granted access to the first data storage but can be prohibited from accessing the second data storage.

According to an embodiment, generating the security code can comprise receiving one or more property values and applying a secure hash algorithm (SHA) on the user-ID and optionally also on one or more first ones of the received property values for generating one or more first hash values. According to some embodiments, a single hash value can be generated from the user-ID alone or from the user-ID and the optionally used first property values. Alternatively, a hash value can be generated for the user-ID and for each of the optionally used first property values, respectively; encrypting the one or more first hash values by the private key for generating one or more encrypted values. The one or more encrypted values can comprise the signature. The signature and one or more second ones of the received property values can be concatenated. The concatenation can provide a concatenated data value. The concatenated data value can be encoded and the encoded data value can be used as the security code. The encoded data value may be a string or 2D code.

Encoding the concatenated value may be advantageous as the encoding may allow representing the signature and one or more property values, including an expiry date, as a short character string that can be entered by a user manually. For example, the encoding algorithm may be a hexadecimal encoding, a Base 64 or a Babble encoding algorithm. It can be a Base32 encoding algorithm. Encoding the security code in form of a 2D code may be based on generating a matrix code, for example, a QR code, or a bar code.

According to an embodiment, the Schnorr algorithm can be used as the secure hash algorithm. This may be advantageous as the Schnorr algorithm can provide safe and short security codes and may thus provide a very good security-usability ratio. The Schnorr algorithm as used herein can be an algorithm for calculating a Schnorr signature algorithm.

According to an embodiment, decrypting can further comprise decoding, by the authentication unit, the received security code. The decoded security code can comprise the signature and one or more property values contained in an un-signed region of the security code. At least one of the property values can be a time value indicating the date when the signature expires. The signature can be decrypted by the public key for returning the at least one first hash value.

According to an embodiment, the matching can comprise calculating at least one second hash value by the authentication unit by applying the same secure hash algorithm as used by the encryption unit at least on the user-ID received by the authentication unit. A current date can be determined by the authentication unit. If the first hash value is equal to the second hash value and if the expiration date has lapsed can be determined. The signature and the security code can be determined to be valid if the first and second hash value are equal and if the expiration date has not lapsed when the authentication unit receives the security code.

The authentication unit receiving the security code can execute a decoding step by a decoding algorithm complementary to the encoding algorithm of the encryption unit for generating the security code. This can mean that encoding any input value with an encoding algorithm and decoding the result of the encoding with a complementary decoding algorithm can return the original input value.

An analysis system can comprise an authentication unit and an analyzer for analyzing biological samples. The authentication unit can control access of a user to one or more functions of the analysis system and can receive a security code and a user-ID of the user via a user-interface of coupled to the authentication unit. The authentication unit can enable access of the user to the analysis system. The security code can be decrypted and if the decrypted security code matches with the user-ID can be determined. If the decrypted security code matches with the user-ID, the user can be authenticated at the authentication unit and an authentication signal can be generated by the authentication unit for permitting the user to initialize at least one function of the analysis system.

An extended analysis system can comprise one or more of the above mentioned analysis systems and an encryption unit. The encryption unit can receive a user-ID of the user and can receive authentication data of the user for authenticating the user at the encryption unit. In case of a successful authentication at the encryption unit, a user-specific security code can be generated taking the user-ID as input and the security code can be outputted for providing the security code to the authenticated user.

An encryption unit can be decoupled from an analysis system. The analysis system can analyze biological samples. The encryption unit can receive a user-ID of a user and can receive authentication data of the user for authenticating the user at the encryption unit. In case of a successful authentication at the encryption unit, a user-specific security code can be generated taking the user-ID as input. The security code can be outputted for providing the security code to the authenticated user. The security code can authenticate the user at the analysis system for permitting the user to initialize at least one function of the analysis system. The expression 'decoupled' as used herein can mean that no ways for automated data exchange between the encryption unit and the analysis system exists, for example due to an absence of a network connection between encryption unit and analysis system.

Figure 2:
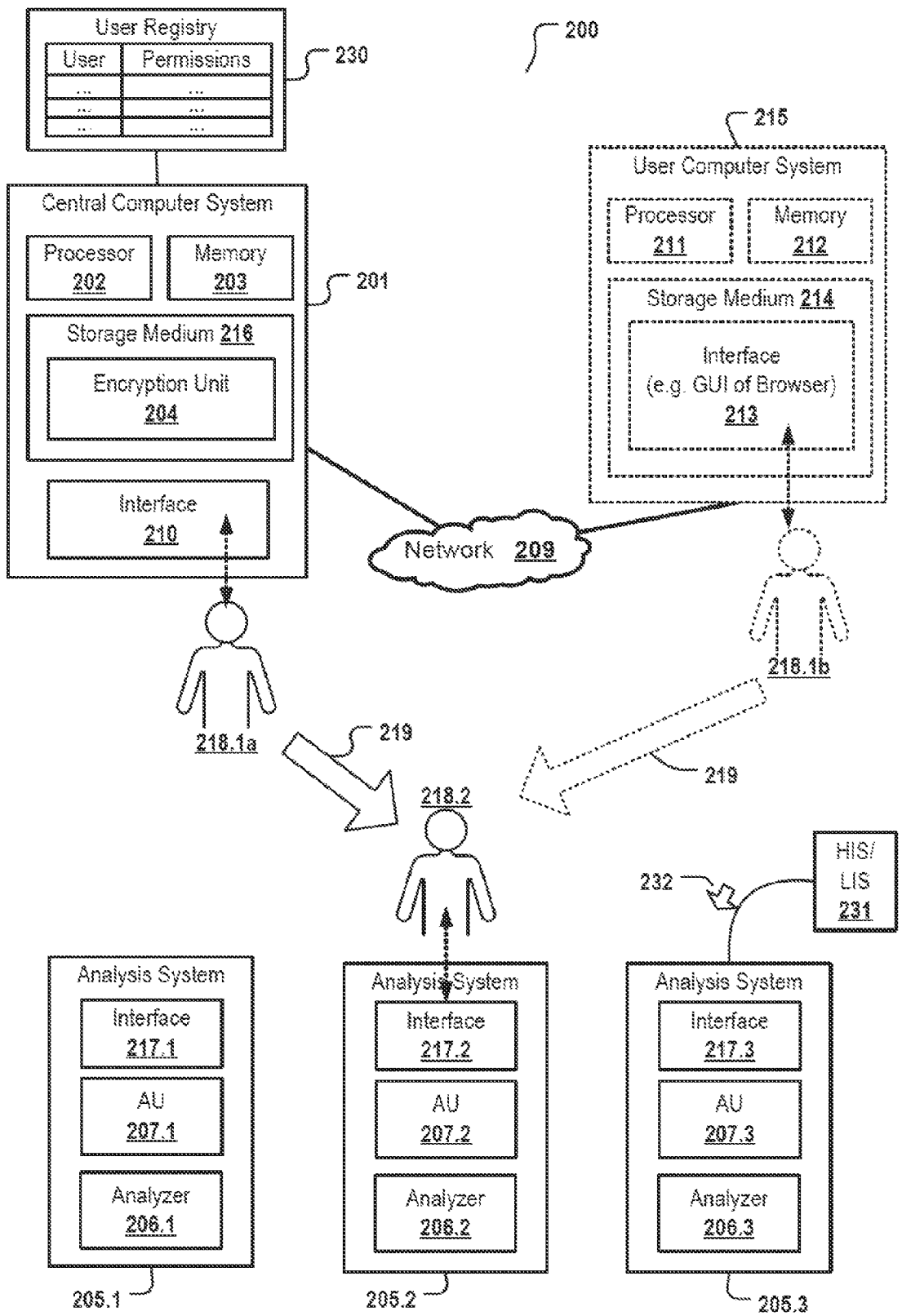
FIG. 2 illustrates a block diagram of an extended analysis system according to an embodiment of the present disclosure.

Referring initially to FIG. 1, FIG. 1 depicts a flowchart of a method whose steps can be executed by components of an extended analysis system as depicted, for example, in FIG. 2. In the following, the method will be described by making reference also to components of FIG. 2.

In a first step 101, an encryption unit 204 can receive authentication data and a user-ID of a user 218. The encryption unit can evaluate in step 102 if the user was able to successfully authenticate at the encryption unit by the authentication data. In case of a successful authentication, the encryption unit can generate in step 103 a user-specific security code. In case the user was not able to authenticate at the encryption unit, the user can be denied access to functionalities of the encryption unit in step 104.

The encryption unit may be an application program running on a central computer system 201 protecting the encryption unit and optionally also other application programs and functions from unauthorized access. Thus, any user having successfully authenticated at the central computer system 201 by some authentication data may automatically also successfully authenticated himself at the encryption unit by the same authentication data. For example, access to the central computer system may be protected by a biometric or password based access control.

After having generated the security code, in the encryption unit can output in step 105 the security code in order to provide the security code to the authenticated user 218. The user may carry the code to the analysis system or may already be at the site of an analysis system when receiving the security code from the encryption unit, for example, via his mobile phone. In step 106, an authentication unit 207 of the analysis system 205 can receive the security code and the user's user-ID via a user interface 217.

The authentication unit having received the security code can decrypt the security code in step 107 and can determine if the decrypted security code matches with the user-ID entered via interface 217. In case it is determined in step 108 that the decrypted security code matches with the entered user-ID, the authentication unit can authenticate the user at the authentication unit in step 109, thereby permitting the user to initialize at least one function of the analysis system 205. In case it is determined in step 108 that the decrypted security code does not match with the user-ID, access to the authentication unit and to functions of the analysis system coupled to the authentication unit can be denied in step 110. In step 111, the user-ID may be forwarded to an auditing unit of the analysis system.

FIG. 2 depicts a block diagram of an extended analysis system 200 comprising an encryption unit 204 and one or more analysis systems 205.1-205.3 respectively comprising an authentication unit 207.1-207.3. The analysis systems may be a standalone analysis systems 207.1-207.3 not connected to any network. Alternatively, it may be connected for example to a laboratory information system (LIS) or laboratory information management system (LIMS) 231 for receiving an analysis request 232. The request may be indicative of a patient whose samples may be analyzed, whereby the indication of the patient can be submitted in pseudonymized form.

The central computer system 201 can comprise a processor 202, a memory 203 and a storage medium 216, for example, an electromagnetic hard disk, a flash drive or the like. The central computer system can comprise an interface 210 allowing a user 218 to enter authentication data to be received by the encryption unit 204. The central computer system 201 may be an isolated, unconnected computer system or may be connected via a network 209 to one or more user-computer systems 215 as shown.

According to some embodiments, the user, for example, a field service representative (FSR), may directly enter his authentication data via interface 210 of the central computer system. For example, the interface 210 may comprise a screen with a graphical user interface (GUI), a keyboard and/or a mouse, a touch screen or the like. This approach can be particularly secure because the authentication data doesn't have to be provided via a network 209, for example, the Internet. The entry of the user-ID of user 218.1a into interface 210 is indicated by the dotted arrow. The central computer system can be coupled to a user registry 230. The user registry can be a database comprising a plurality of user-IDs respectively having assigned an authentication data reference value which may be used for comparison with the received authentication data for authenticating the user at the encryption unit. Each user-ID may be assigned some permissions which may be evaluated during the generation of the security code for determining the kind of analysis system and/or the kind of function the user may be granted access to or may be allowed to execute. The user registry may further comprise an assignment of one or more property values to each of the user-IDs in the registry. These properties may be included in the security code and may control the execution of the at least one function.

According to other embodiments, a man-machine interface 213 of a user-computer system 215 may be used for entering the authorization data and the user-ID and for submitting the entered data and ID via network 209 to the encryption unit 204. Interface 213 may be a graphical user interface displaying a dialog window generated for example, by a browser operable to transmit the entered authentication data and user-ID of user 218.1b to the encryption units, for example by HTTP get or post requests. The user-computer system 215, its components and the user 218.1b entering authentication data via interface 213 are depicted by dotted boxes. User 218.1a and user 218.1b may actually be the same user authenticating at the encryption unit according to a first 218.1a and second 218.1b use-case scenario. In the following, user 218 in the first use case scenario can be referred to as 218.1a, in the second use case scenario as user 218.1b. In the first use-case scenario, the user 218.1a can enter his user credentials directly in the encryption unit of the central computer system. In another use-case scenario, the user 218.1b can enter his user credentials (authorization data and user-ID) via an intermediate user-computer system.

The encryption unit 204 can take the user-ID as input in order to generate a security code being a derivative of the user-ID. The generated security code may be output via interface 210 to user 218.1a. For example, interface 210 may be a GUI comprising a dialog window which can display the generated security code. Alternatively, the encryption unit may generate a printout by a printer coupled to the encryption unit. Alternatively, or in addition, the security code can be submitted to a mobile processing device, for example, a mobile phone, of the user.

In case the user 218.1b uses the user-computer system 215 for entering his user-ID, the security code generated by the encryption units can be submitted via network 209 to the interface 213 of user-computer system 215. Interface 213 may output the security code to user 218.1b. Interface 213 may be a screen showing a browser displaying the security code contained in a web-site generated by the central computer system. Alternatively, the received security code can be output by the user-computer system 215 as a printout displaying the security code and/or is output by sending the security code from the user-computer system 215 to a mobile processing device of user 218.1b.

The user 218 may move to one of the analysis systems 205.1-205.3 as indicated by arrows 219. The use-case scenario corresponding to user 218.1b depicted in dotted lines can indicate that the user requests and/or receives the security code via his user-computer system. According to an embodiment, the encryption unit may receive authentication data and/or output the security code exclusively via an interface 210 of the central computer system, exclusively via one or more interfaces 213 of user-computer systems, or via both types of interfaces 210, 213.

By entering the user-id and security code via interface 217.2 into authentication unit 207.2 of an analysis system 205.2, the user 218.2 may authenticate at the authentication unit and the analyzer 206.02 and/or other components of the analysis system, thereby being permitted to initiate the execution of one or more functions of the analysis system 205.2.

Figure 3:
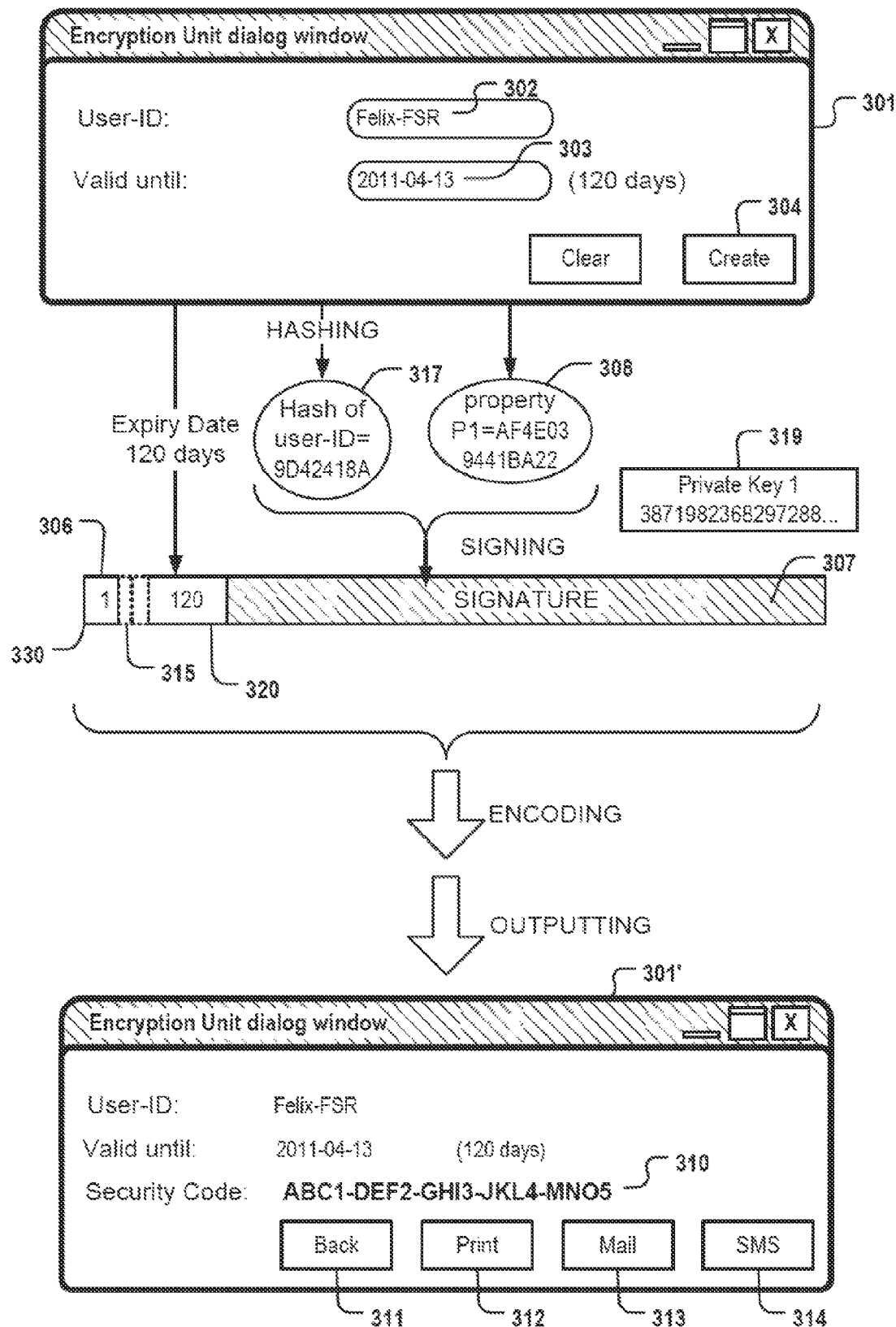
FIG. 3 illustrates the generation of a security code according to an embodiment of the present disclosure.

FIG. 3 shows a user interface 210 implemented as a graphical user interface (GUI) provided by the encryption unit 204. The graphic user interface can comprise a dialog window 301 allowing a user having authenticated at the encryption unit to manually enter his user-ID. Alternatively, the dialog window may comprise GUI elements for entering the user-ID and the authentication data. The window 301 can comprise an editable GUI element for entering the user-ID 302 and optionally a further editable GUI element for specifying an expiry date 303 of the signature of the security code to be generated by the encryption unit. Alternatively, the expiry date may be a predefined or automatically generated data value provided by the encryption unit 204. After having submitted the entered data to the encryption unit, for example, upon having clicked on the create button 304, a hash value 317 can be generated from the entered user-ID 302. In addition, a private key 319 can be used by the encryption unit for calculating a signature 307 from the hash value 317. Optionally, the signature may be calculated by taking, in addition to the hash value 317, one or more property values 308 as input. One of the property values may be the expiry date.

The signature, the expiry date 320, one or more optional property values 315 and a key index 306 provided automatically by the encryption unit can be concatenated for generating an intermediate, concatenated data structure 330 comprising the signature 307. Depending on the embodiment, the optional property values may be contained in one or more non-encrypted sections of data structure 330 and/or may be contained within the signature 307 as is the case, for example, for property value 308. The property values may be provided automatically by the encryption unit. The expiry date 320 may be included in the encrypted section 307 and/or in the non-encrypted section 306, 315, 320 of the data structure 330. Security-relevant property values such as the expiration date may be contained in the encrypted code section and in addition in an un-encrypted code section of the security code. Decrypting the encrypted copy of the expiration date and comparing it with the unencrypted copy in the security code may ensure that the expiration date was not modified after the encryption step.

After generated the intermediate data structure 330, the whole data structure or at least the encrypted section 307 (i.e., the signature) of the data structure can be used as input of an encoding algorithm for generating a security code 310. The encoded section of the intermediate data structure 330 can comprise at least the encrypted user-ID or a derivative thereof. The expiry date may be part of the encrypted or non-encrypted data structure section. The security code can be output and be provided to the user 218. For example, the encryption unit may generate an updated version 301' of the dialog window displaying the security code 310. In addition, the dialog window 301' may display the expiry date and/or remaining days of validity of the security code. Further, the dialog window 301' may comprise selectable GUI elements 311-314. In case the user selects one of the GUI elements, the encryption unit can send the security code via the communication channel represented by the selected GUI element. For example, the security code can be submitted via e-mail to a mailbox of the user in case button 313 is selected or via SMS to a mobile phone of the user in case button 314 is selected. In case button 312 is selected, a printout displaying the security code can be generated by a printer coupled to the encryption unit or, in case the security code is transmitted via a network to a user-computer system 125, by a printer coupled to the user-computer system. The user may carry the output security code to the analysis system he wants to authenticate at or may request the security code via a mobile processing device when having arrived at the analysis system. The authentication of the user at an authentication unit of an analysis system by the output security code is depicted in FIG. 4.

Figure 4:
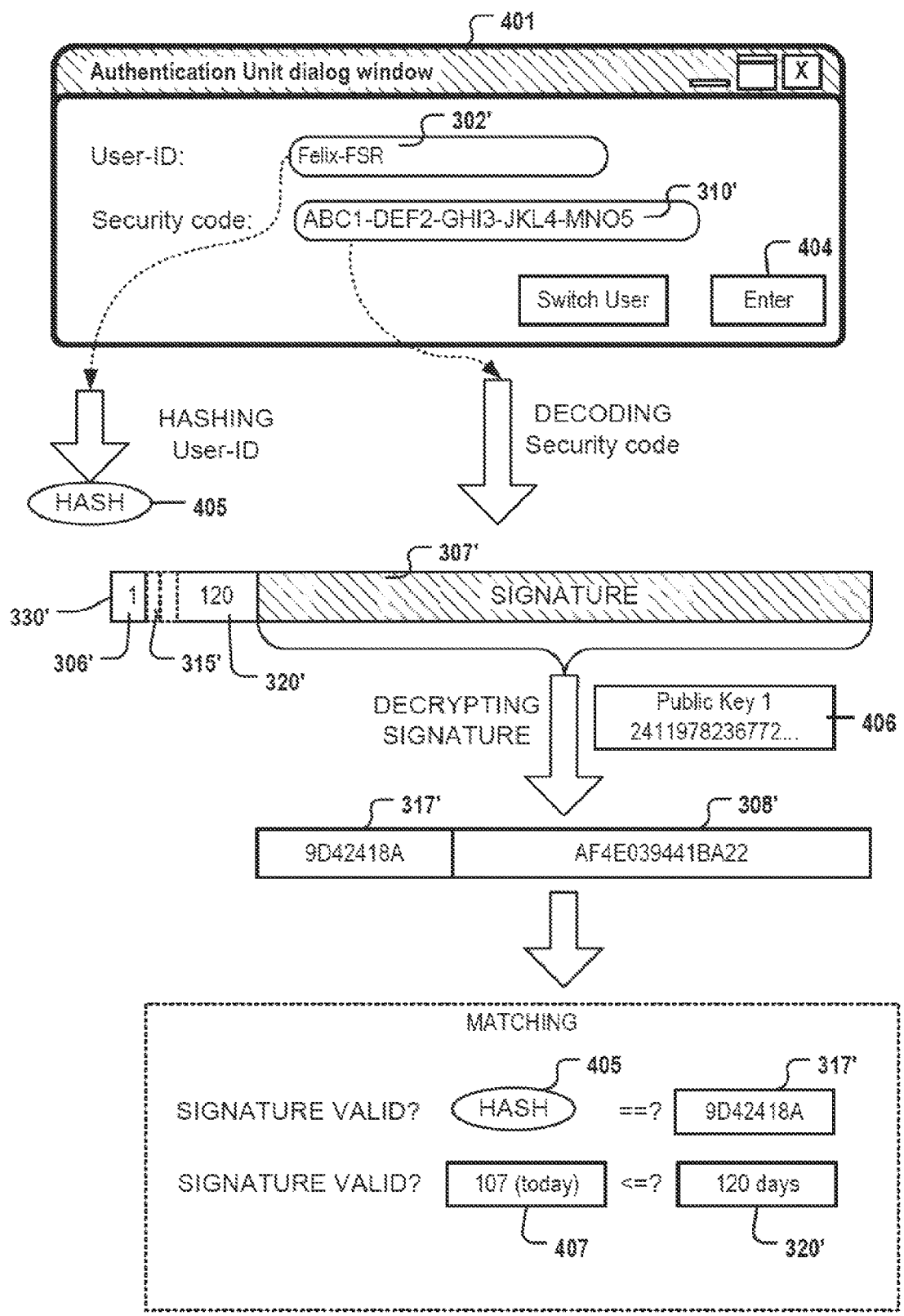
FIG. 4 illustrates the decoding and decryption of the security code according to an embodiment of the present disclosure.

FIG. 4 shows a dialog window 401 of a graphical user interface 217.2 generated by an authentication unit 207.2 of an analysis system 205.2. The dialog window 401 can comprise an editable GUI element, for example, a text field, allowing a user to enter his user-ID 302. Upon a selection of the button 404 by the user, the entered user-ID and the entered security code can be received by the authentication unit 207.2. The authentication unit can calculate a hash value 405 from the entered user-ID 302 and can execute a decoding operation on the received security code, thereby generating a decoded intermediate data structure 330'. The hashing algorithm used by the encryption unit and the hashing algorithm used by any one of the authentication units may have to be identical. The authentication unit can decrypt the signature 307' by a public key 406. The public key 406 and the private key 319 having been used for generating the signature can constitute an asymmetric cryptographic key pair. When executing the matching, the authentication unit can compare the hash value 405 calculated by the authentication unit from the user-ID received via the dialog window 401 with the hash value 317' extracted from the signature 307' of the security code 310' by the public key 406. In addition, the authentication unit can determine a current date 407 and can check if the expiration date 320' contained in the security code 310 has lapsed. In case the compared hash values 405 and 317' are equal and the expiration date 320' has not lapsed, the signature 307' and the security code 310' can be considered valid and the user can be allowed to execute one or more functions of the analysis system. Optionally, the authentication unit may extract one or more property values 315', 308' for determining which ones of the available functions the user may be allowed to execute.

The embodiments depicted in FIGS. 3 and 4 can comprise an encoding and decoding step for generating and evaluating the security code. According to an embodiment, not applying encoding and decoding steps, the intermediate data structure 330, 330' may be used as the security code.

Figure 5:
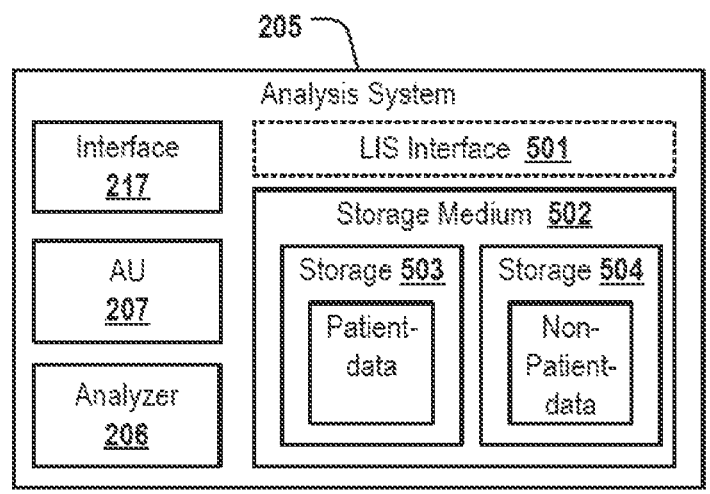
FIG. 5 illustrates a block diagram of an analysis system with two storage units according to an embodiment of the present disclosure.

FIG. 5 depicts an analysis system 205 comprising a first 504 and a second 503 data storage, wherein the first data storage can comprise non-patient data, in particular technical information allowing the user to configure the analysis system or execute the at least one function in accordance with the technical information. The second data storage may comprise patient data or other kind of data the user may not be permitted to access. The analysis system may optionally also comprise an interface 501 for receiving an analysis request from the LIS.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analysis system, the analysis system comprising:
   an analyzer for analyzing biological samples; and
   an authentication unit, wherein the authentication unit controls access of a user to one or more functions of the analysis system, wherein the authentication unit receives a security code and a user-ID of the user via a user-interface coupled to the authentication unit, wherein the security code and the user-ID are entered by the user, wherein the authentication unit enables access of the user to the analysis system, wherein the authentication unit decrypts the security code and determines if the decrypted security code matches with the user-ID, wherein the matching encompasses a check if the security code comprises the user-ID in encrypted form, and wherein if the decrypted security code matches with the user-ID, the authentication unit authenticates the user at the authentication unit and generates an authentication signal by the authentication unit for permitting the user to initialize at least one function of the analysis system, wherein the at least one function is selected from a group comprising: unlocking a reversibly lockable hardware component of the analysis system for permitting the user to access the hardware component; replenishing solid consumables of the analysis system or permitting the user to replenish the solid consumables; refilling liquid consumables of the analysis system or permitting the user to refill the liquid consumables; updating an application program used for maintaining or controlling the analysis system or permitting the user to execute the update; repairing an error state of the analysis system or permitting the user to execute the repair; execute a calibration by the analysis system or permitting the user to execute the calibration; and combinations thereof.

2. An extended analysis system, the extended analysis system comprising:
one or more analysis systems according to claim 1; and
an encryption unit for receiving a user-ID of the user and receiving authentication data of the user for authenticating the user at the encryption unit; in the case of a successful authentication at the encryption unit, generating a user-specific security code, thereby using an encryption algorithm and taking the user-ID as input, whereby the user-ID is stored in the security code only in encrypted form; and outputting the security code for providing the security code to the authenticated user.

3. The analysis system according to claim 1, wherein the security code comprises a signature of the user-ID or a derivative thereof.

4. The analysis system according to claim 3, wherein the security code comprises the signature and an analysis system-type-ID indicative of a type of analysis system at which the authenticated user is selectively allowed to execute the at least one function.

5. The analysis system according to claim 3, wherein the security code comprises the signature and a time value indicative of a date when the signature expires.

6. The analysis system according to claim 1, further comprising,
a reader coupled to the authentication unit to read a displayed security code.

7. The analysis system according to claim 1, further comprising,
an encryption unit with a dialog window, wherein the dialog window allows the user to enter the user-ID, and upon entry of at least the user-ID, displays the security code.

8. The analysis system according to claim 7, wherein the encryption unit further displays, one or more GUI elements to the user, wherein the GUI elements allow the user to select one of a set of data transmission techniques comprising: sending the security code via an SMS to a mobile processing device of the user; storing the security code on a portable storage medium; generating a paper-based printout of the security code; sending an e-mail to a mailbox of the user, wherein the e-mail comprises the security code; and combinations thereof.

9. The analysis system according to claim 1, wherein the authentication unit of the analysis system is restricted to provide access to non-patient data only.

10. The analysis system according to claim 1, wherein the user-ID is a user-ID provided and managed by an operating system, wherein the operating system constitutes a runtime environment of the authentication unit.

11. The analysis system according to claim 1, further comprising,
a first data storage can comprising non-patient data.

12. The analysis system according to claim 11, wherein the non-patient data comprises technical information allowing the user to configure the analysis system or execute the at least one function in accordance with the technical information.

13. The analysis system according to claim 1, further comprising,
a second data storage comprising data the user is not be permitted to access.

14. The analysis system according to claim 13, wherein the data is patient data.

15. The analysis system according to claim 1, further comprising,
an interface for receiving an analysis request from the LIS.

* * * * *